United States Patent [19]

Simon et al.

[11] Patent Number: 5,578,271

[45] Date of Patent: Nov. 26, 1996

[54] TANDEM PHOTOIONIZATION DETECTOR AND HALOGEN SPECIFIC DETECTOR

[75] Inventors: Richard K. Simon; Michael L. Duffy; Michael J. Tanner, all of College Station; Mathias N. Barringer; Nathan C. Rawls, both of Bryan, all of Tex.

[73] Assignee: O.I. Corporation, College Station, Tex.

[21] Appl. No.: 397,437

[22] Filed: Mar. 1, 1995

[51] Int. Cl.$^6$ .................. G01N 27/00; G01N 21/00
[52] U.S. Cl. .................. 422/98; 422/54; 422/83; 422/90; 422/91
[58] Field of Search .................. 422/54, 83, 89, 422/90, 91, 94, 95, 98

[56] References Cited

U.S. PATENT DOCUMENTS

| | | | |
|---|---|---|---|
| 3,423,181 | 1/1969 | Dimick et al. | 422/54 |
| 3,535,088 | 10/1970 | Zimmermann | 422/54 |
| 3,615,237 | 10/1971 | Speakman | 422/54 |
| 4,524,047 | 6/1985 | Patterson | 422/98 |
| 4,555,383 | 11/1985 | Hall | 422/89 |
| 4,804,846 | 2/1989 | Hall | 250/379 |
| 4,999,162 | 3/1991 | Wells et al. | 422/54 |
| 5,019,517 | 5/1991 | Coulson | 422/89 X |

FOREIGN PATENT DOCUMENTS 2738608  3/1979  Germany .................. 422/54

OTHER PUBLICATIONS

H. Sonobe et al, *J. Agric. Food Chem.* 1980, 28, 265–269.
H. Roseboom et al, *J. Chromatog.* 1980, 202, 431–438.
F. J. Reineke et al. *J. Chromatog.* 1985, 323, 323–329.
P. L. Patterson *Lipids* 1985, 20, 503–509.
T. Ramstad et al. *Analyst* 1992, 117, 1361–1366.
F. Herman *Anal. Chem.* 1993, 65, 1023–1027.

*Primary Examiner*—Arlen Soderquist
*Attorney, Agent, or Firm*—Arnold, White & Durkee

[57] ABSTRACT

A photoionization detector (PID) and an improved halogen specific detector are disclosed, for direct connection of the PID outlet to the halogen specific detector inlet. The tandem detector is used for detection of volatile organic compounds and the like. A jet assembly and seal between the PID and halogen specific detector provide a leak free and upswept dead volume-free connection between the two detectors.

1 Claim, 11 Drawing Sheets

TANDEM PHOTOIONIZATION DETECTOR AND HALOGEN SPECIFIC DETECTOR

BACKGROUND OF THE INVENTION

1. Field of the Invention

This invention relates generally to detectors for gas chromatography, continuous emission monitoring, and other types of devices used for field sampling of volatile organic compounds and the like. More specifically, the invention relates to a halogen specific detector and a direct connection between the halogen specific detector and a photoionization detector.

2. Description of the Related Art

A photoionization detector (PID) is a well known detector which generates a current due to photoionization of the analyte passing through the device. In the PID, the analyte absorbs radiation, typically in the ultra violet (UV) region of the electromagnetic spectrum, which causes the analyte to ionize into an electron and positive ion pair. Within the PID two or more electrodes are present which provide an extraction field and permit quantitation of the generated current. The light source can consist of UV generating lamps (DC, AC, inductively, or capacitively coupled or otherwise modulated power to create UV radiation passing through one or more windows which serve to limit the band of radiation passing into the PID), or can consist of a windowless design in which UV radiation at frequencies above that which can be transmitted through a window is utilized as the radiation source. The electrodes are positioned to minimize UV light from striking them, generating photoelectrons which can be a source of unwanted background current and noise. Additional electrode(s) can be used to serve as guard electrode(s) which serve to minimize leakage currents between the sensing electrodes.

A halogen specific detector is a thermionic device related to the work done by Rice (U.S. Pat. No. 2,550,498), and Roberts (U.S. Pat. No. 2,795,716). The Rice patent entitled "Method and Apparatus for Detecting Vapors and the Like" discloses directly heated anodic and cathodic structures, with the anodic structure being activated with an alkali containing salt. According to Rice, the precise theory of operation is not completely understood. The mechanism proposed by Rice indicates that alkali sensitizes a heated anode structure. The collision of chlorine (neutral) with the alkali results in a large current of positive alkali ions being emitted with the energy being supplied by the formation of an alkali halide on the anode surface. It appears that the response of the Rice detector functions by a stimulated alkali emission from an anodic structure. The Roberts patent discloses a device having similar principles of operation as Rice, and also discloses a central core around which one of the electrode structures is placed.

The response of the halogen specific detectors of Rice and Roberts have problems with stability, excessive broadening of chromatographic peaks, and sensitivity to the type and class of compound containing the halogen. With those type of detectors, the compounds oxidized at the heated surfaces, i.e., the anodic and/or cathodic structure. Therefore, these detectors were unreliable because of differences in oxidation rates of different types and/or classes of compounds (i.e., the differences in molecular structure), resulting in different efficiencies of generating free halogens. However, these types of detectors were useful for leak detection and similar uses where analysis time was relatively unimportant, and for applications where it was relatively unimportant to detect and distinguish several compounds from one sample.

Rice and Roberts are in direct contrast to the detectors proposed by Arimoto, Fujii, and Jimba regarding a (positive) surface ionization detector (J. Chromat., 355(1986)375–382, Anal. Chem., 62 (1990)107, and European Patent Application WO 86/06836), and that of Coulson (U.S. Pat. No. 5,019,517).

Coulson (U.S. Pat. No. 5,019,517) discloses a halogen specific detector in which the sensor's cathode is required to be "substantially alkali free", and requires the use of a temperature sensor in either the pyrolysis body or as part of the probe assembly, with temperature control being maintained by monitoring the temperature of the sensor. Attempts to operate a halogen specific detector as described in U.S. Pat. No. 5,019,517 utilizing high purity alumina structures or quartz structures (devoid of alkali metals) have failed to generate a reproducible response to halogens, in the absence of an alkali glass ceramic for the anode structure (as taught by Rice and Roberts).

In the past, photoionization detectors (PIDs) and electrolytic conductivity detectors (EICDs) have been connected in series to allow use of the same sample twice and to reduce the time required to do the analysis of specific compounds. Additionally, the PID and EICD have different abilities to detect certain types of compounds, and it is desirable to use each type of detector to detect and quantitate samples. Serial connection of the PID-EICD for independently mounted detectors was through a transfer line (typically heated to prevent condensation) and routed from the outlet of the PID into the GC oven and then into the EICD inlet port (or other alternate connector). Serial connection has limitations because of leaks between connections, cold spots (condensation of analyte), adsorption of analyte on active sites, reaction of analyte on reactive materials within the transfer line, and the occupation of two detector mounting sites (in a two detector gas chromatograph)-preventing the use of a third detector.

More recently, electrolytic conductivity detectors (EICDs) have been directly coupled to photoionization detectors (PIDs as is disclosed by U.S. Pat. No. 4,805,846 (Hall).

However, halogen specific detectors have been used as stand-alone detectors only. They have not been connected serially or in tandem with other detectors such as PIDs.

SUMMARY OF THE INVENTION

The present invention provides an improved halogen specific detector that may be operated sequentially with a PID when coupled in tandem. One purpose of the present invention is to provide a halogen specific detector with better quantitation of halogen species and improved chromatographic peak shape. Another purpose of the invention is to couple a PID to a halogen specific detector to eliminate an external heated transfer line which would otherwise be required for the sequential (i.e., series) operation.

DESCRIPTION OF A PREFERRED EMBODIMENT

Figure 1:
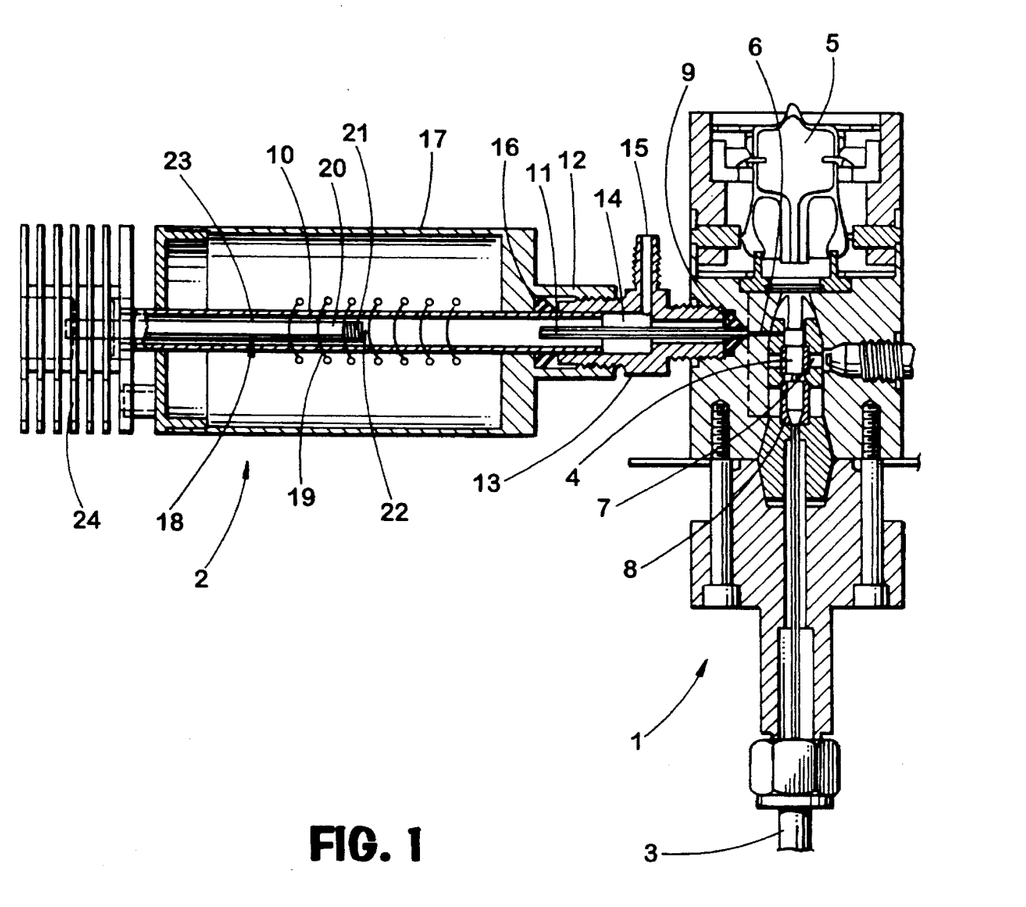
FIG. 1 is a section view of the halogen specific detector and photoionization detector according to a preferred embodiment of the present invention.
Figure 2:
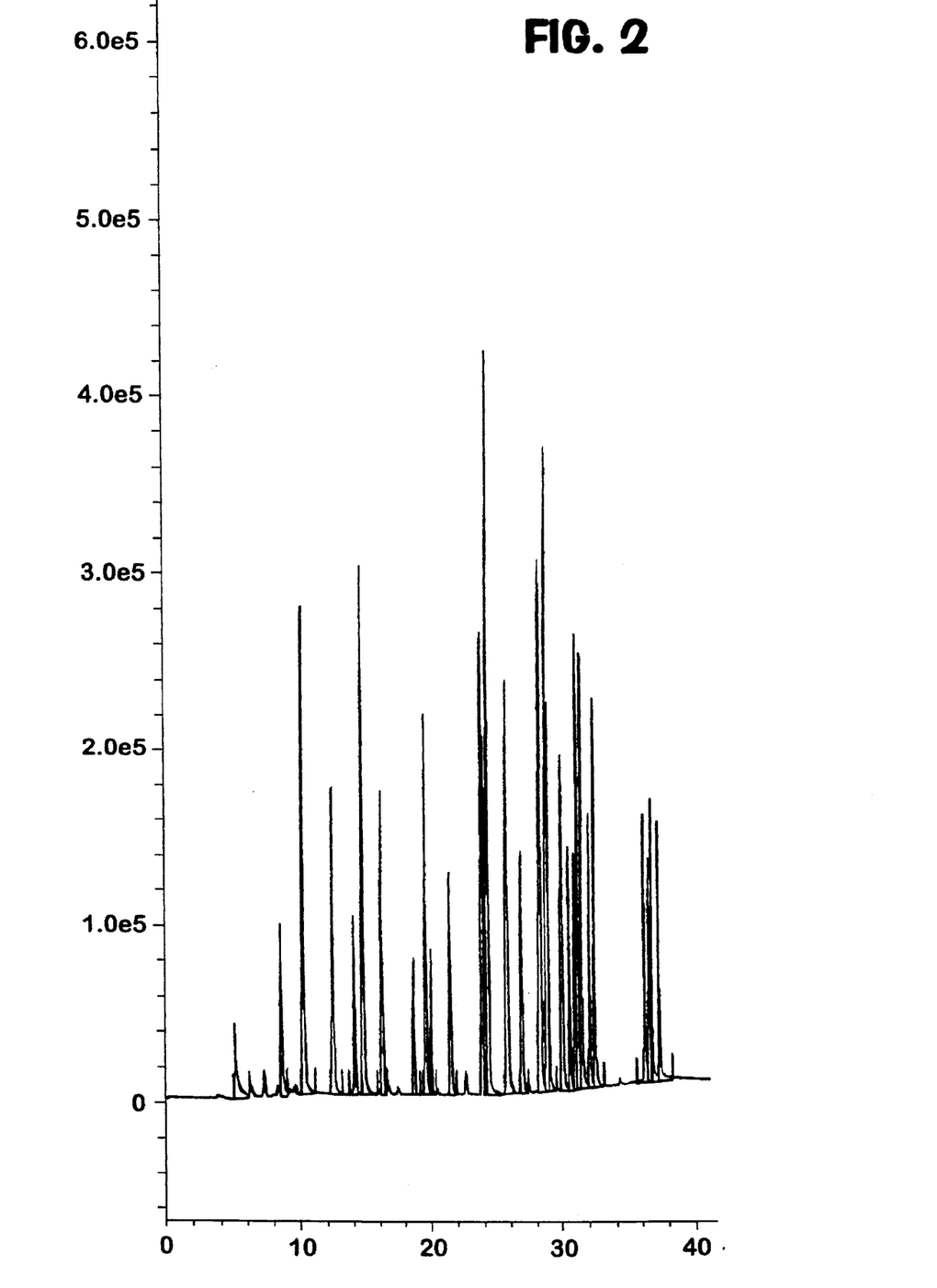
FIGS. 2 and 3 are a PID response and a halogen specific detector response, respectively, to EPA test series 502.2, using the tandem system of the present invention, with the halogen specific detector reactor temperature held at 1000° C. (1273° K.).
Figure 3:
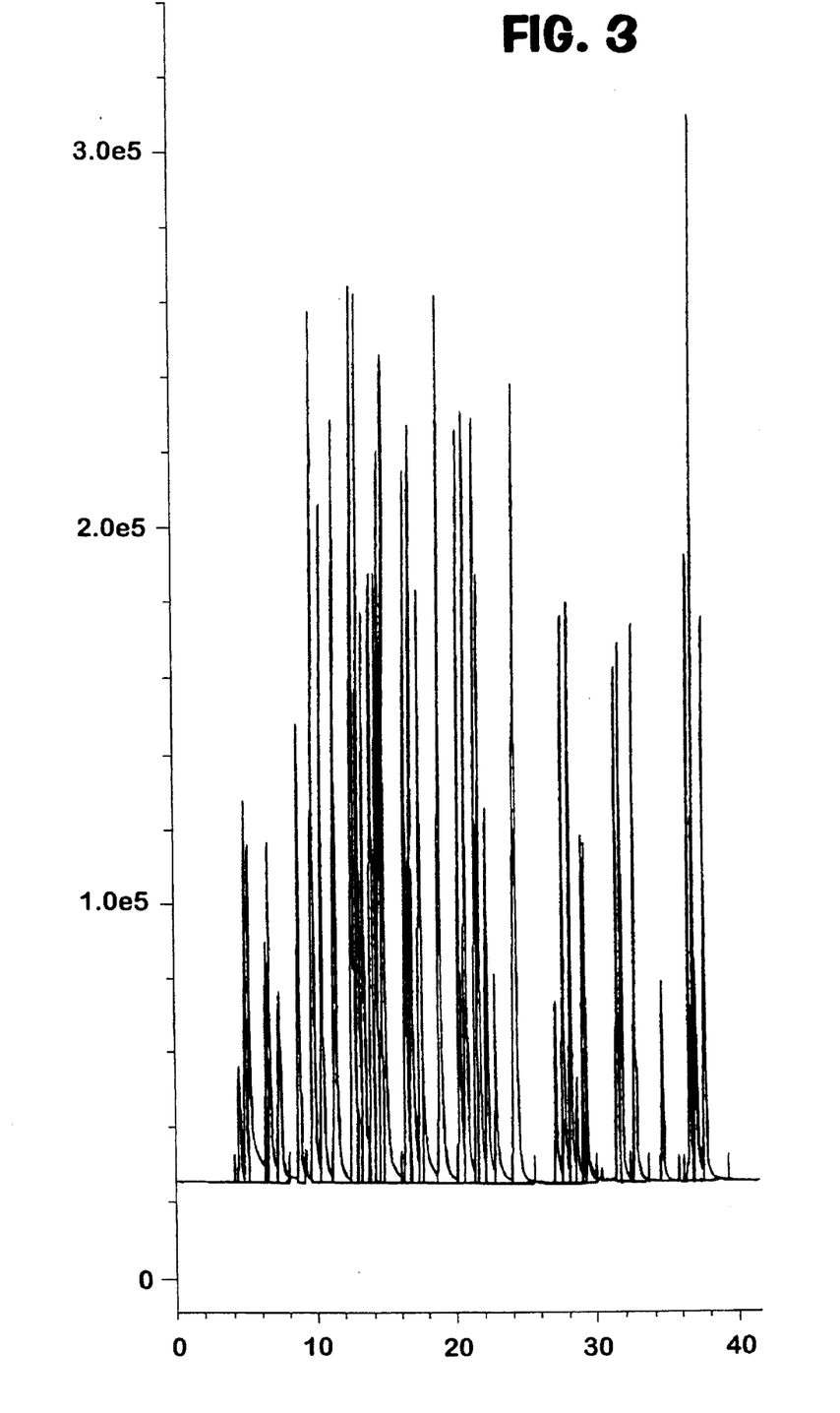
Figure 4:
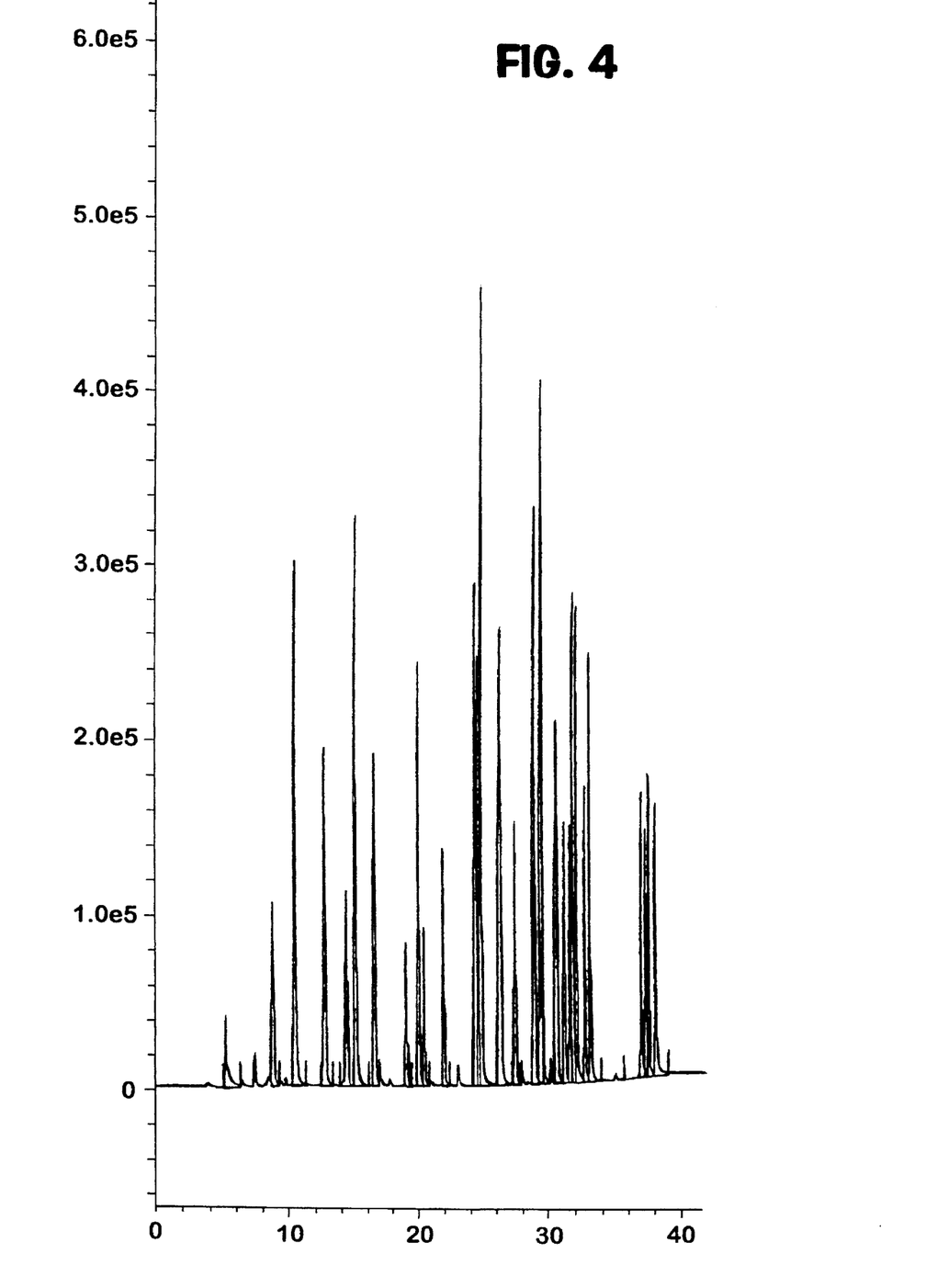
FIGS. 4 and 5 are a PID response and a halogen specific detector response, respectively, to EPA test series 502.2, using the tandem system of the present invention, with the halogen specific detector reactor temperature held at 1100° C. (1373° K.).
Figure 5:
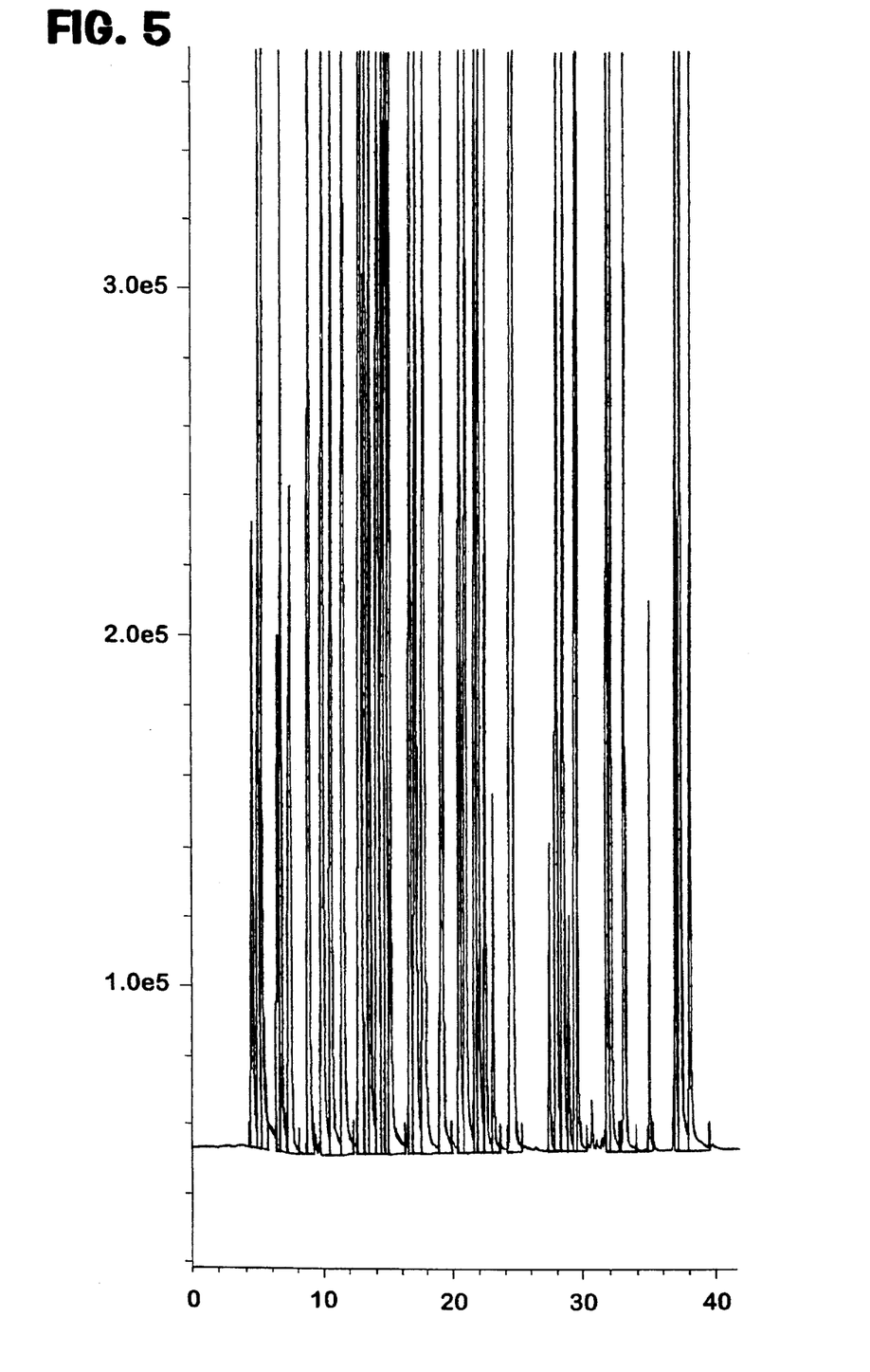
Figure 6:
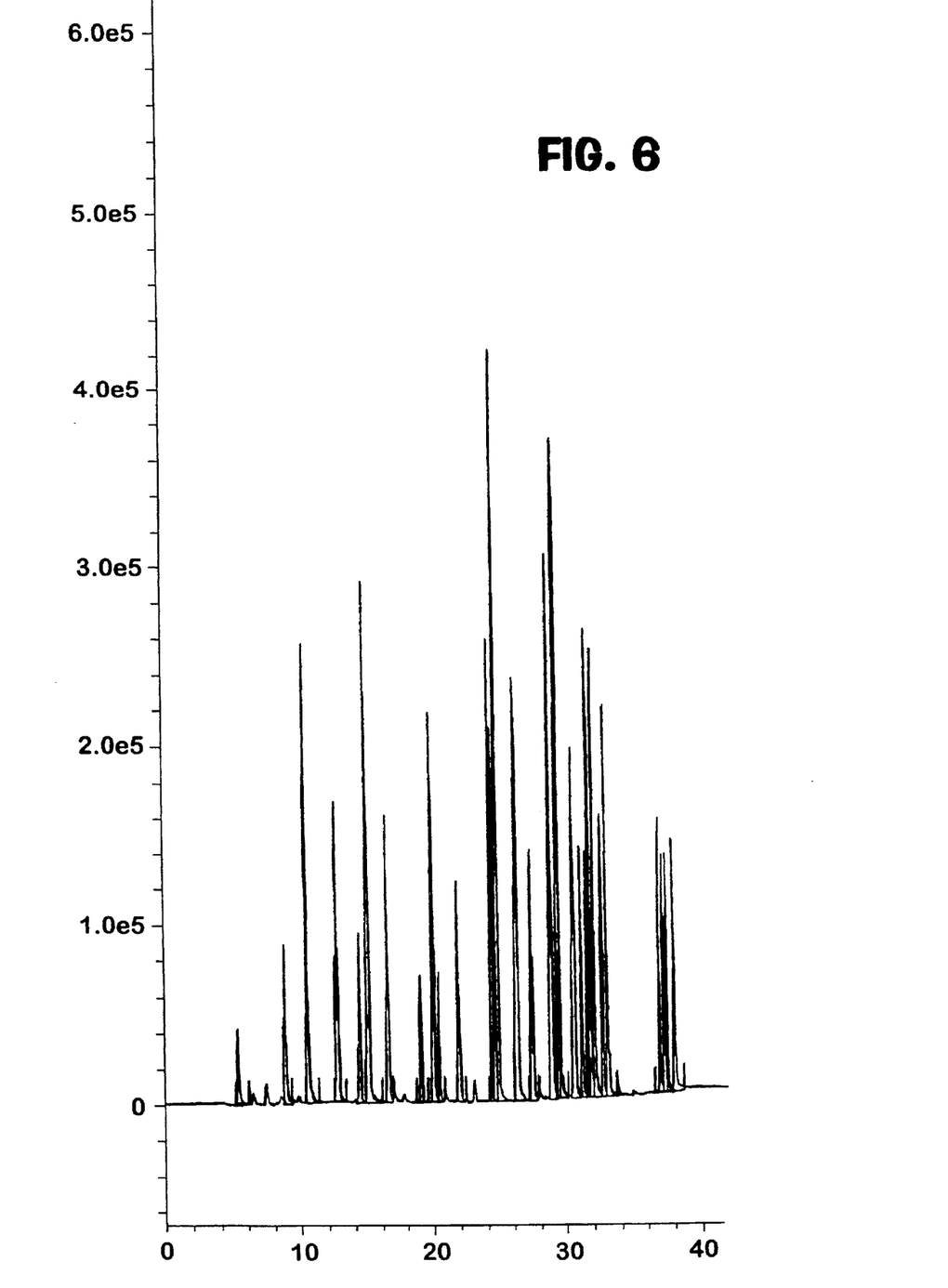
FIGS. 6 and 7 are a PID response and a halogen specific detector response, respectively, to EPA test series 502.2, using the tandem system of the present invention, with the halogen specific detector reactor temperature held at 900° C. (1173° K.).
Figure 7:
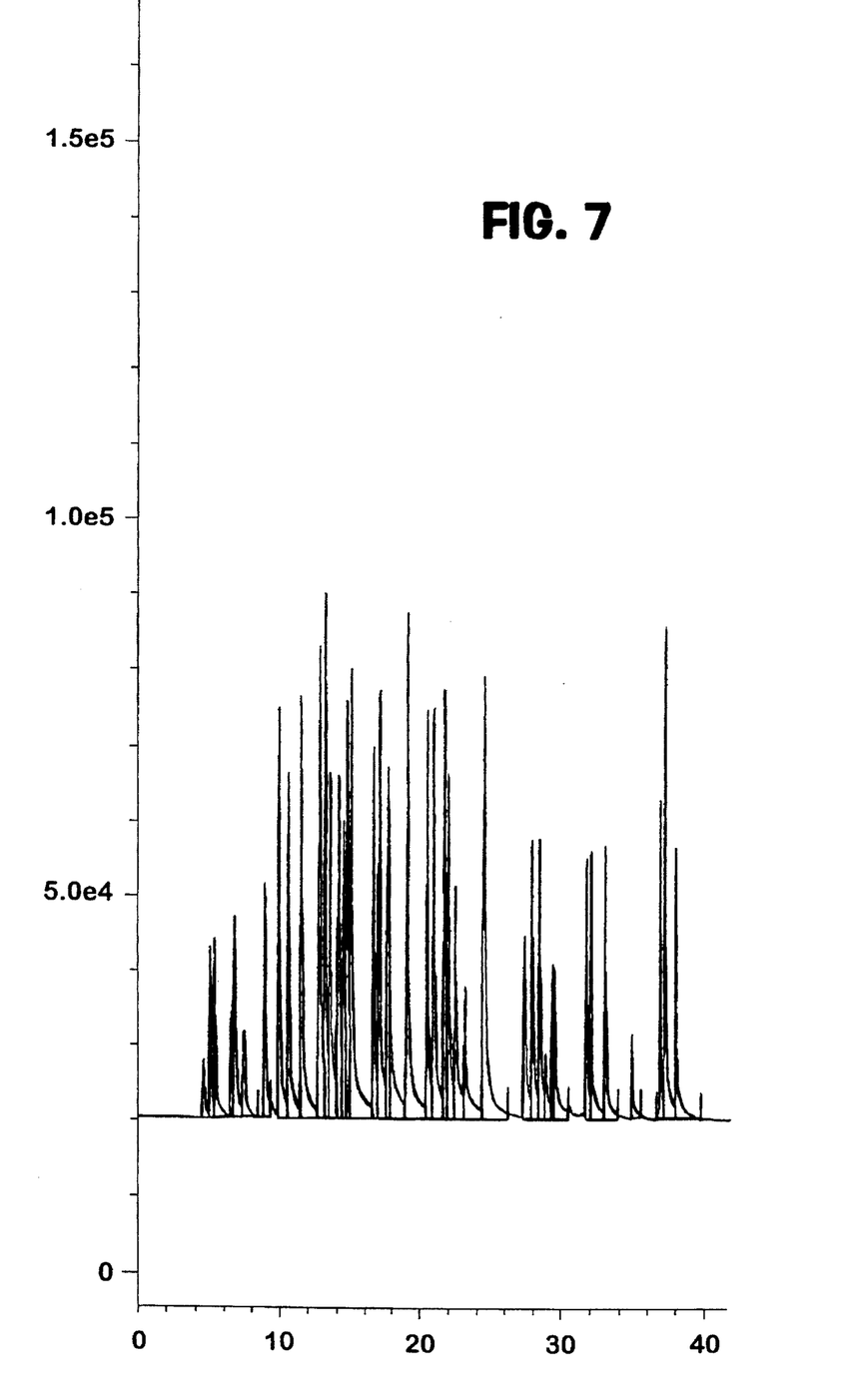

FIG. 1 shows a photoionization detector (PID) 1 coupled to a halogen specific detector 2 according to a preferred embodiment of the present invention. The sample input to the tandem PID/halogen specific detector may be an effluent stream from a GC, a gas sampling stream, a sample from part of a gas leak detector, or a sample from a process stream detector. The sample may be introduced by actively pumping (i.e., positive pressure delivery at the inlet of the PID) the sample or pulling (i.e., vacuum pump at outlet of the halogen specific detector) the sample into the tandem PID/halogen specific detector. The tandem PID/halogen specific detector can also be connected to pre-concentration devices, with the tandem configuration being utilized as a screening tool for determining presence or absence of compounds which generate a response in the PID and/or halogen specific detector.

In a preferred embodiment, as shown in FIG. 1, the PID is manufactured by O.I. Corporation of College Station, Tex. However, the PID for use in the present invention can be any PID which can be adapted to serve as a base for the halogen specific detector with direct coupling of the exit port of the PID with the halogen specific detector inlet port (via inert jet or otherwise directly coupled). The choice of PID that may be utilized is independent of the type or style of light source, source of energizing power for the light source, light source with window or without window, multiple electrodes (2 or more), bias and current extraction modes, pulsed sample injection into the PID, pressure present in PID cell, electrode geometry, and the presence (or lack of) a sweep gas for the lamp window or light source volume.

The PID has at least one inlet port 3, an ionization chamber 4, a light source 5, and an exit port 6. The inlet port is utilized to input analyte into the ionization chamber for quantitation. The ionization chamber contains at least two electrodes 7, 8 for generation of an extraction field and connection to a current measuring circuit. The light source is used to introduce light (typically in the ultraviolet section of the electromagnetic spectrum). At least one exit port is also required to permit analyte to exit the ionization chamber. The exit port is directly coupled with the halogen specific detector without leakage or additional unswept dead volume.

It is essential that the connection between the PID and halogen specific detector be leakage free. Therefore, in a preferred embodiment the inlet of the halogen specific detector is externally threaded into the exit port of the PID, and sealed with a graphite or graphite-vespel ferrule 9 inserted at the connection.

The halogen specific detector utilizes a connecting pathway from the ionization chamber of the PID into the reactor core 10 which can be a direct connection with the PID, or preferably directed via inert jet assembly 11 into the reactor core. The purpose of the jet assembly is to minimize band broadening which can occur when transferring the analyte from the PID into the halogen specific detector. The jet assembly is a tube preferably made of high purity alumina or glass lined tubing, but also may be quartz tubing. In a preferred embodiment, the jet assembly is 1.25 inches in length, 0.0625 inches in outer diameter and 0.030 inches in inner diameter, and is more than 99% purity alumina.

The jet assembly is positioned within inlet port or coupling connector 13, which is externally threaded to the internally threaded inlet end 12 of the halogen specific detector, with ferrule 16 therebetween. The jet assembly extends outwardly from the inlet port or coupling connector through the seal (ferrule 9) to exit port 6 of the PID. Thus, the jet assembly and seal provide a leak free and upswept dead volume-free connection between the PID and halogen specific detector.

The coupling connector 13 includes a cavity 14 communicating with auxiliary air or oxygen source inlet port 15. The flow of oxygen or air through this port provides gas flow into the reactor core for oxidative pyrolysis, and prevents back diffusion of analyte into the dead volume in cavity 14 between the outer wall of the jet and the inner wall of the coupling connector.

Figure 8:
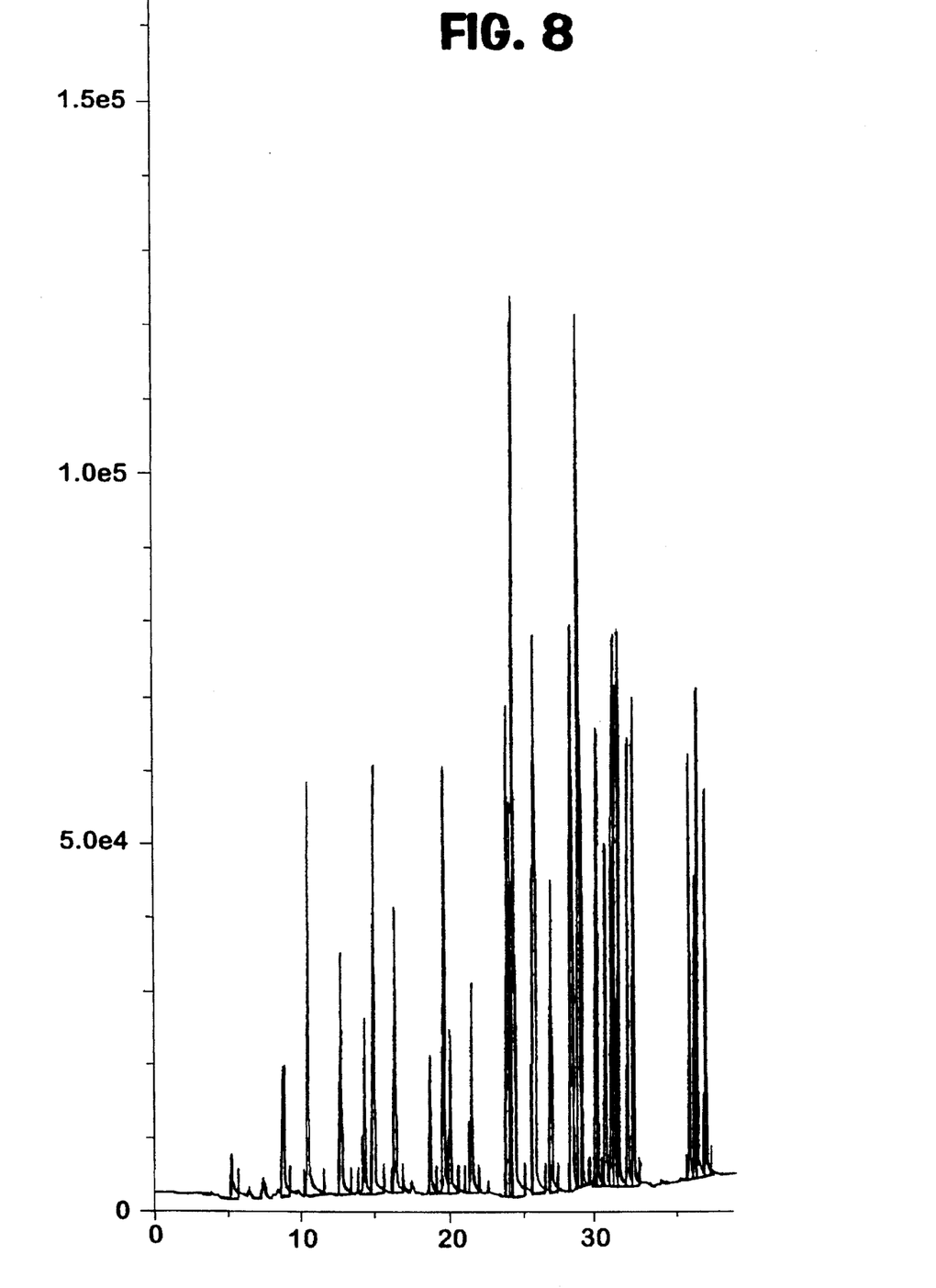
FIGS. 8 and 9 are a PID response and a halogen specific detector response, respectively, to EPA test series 502.2, using the tandem system of the present invention, with the halogen specific detector reactor temperature held at 1000° C. (1273° C.), and air (at 15 ml/min) flowing into the PID.
Figure 9:
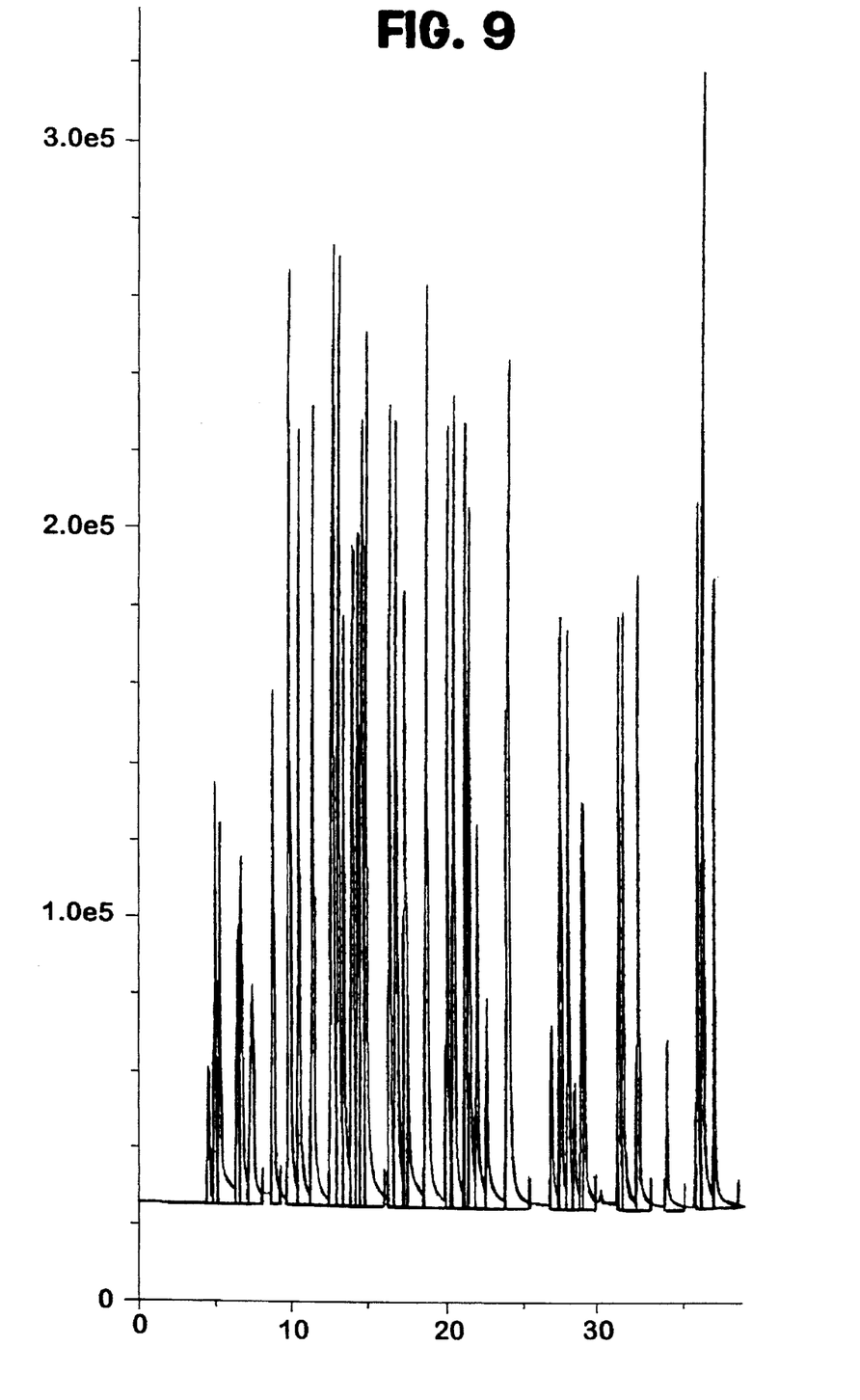
Figure 10:
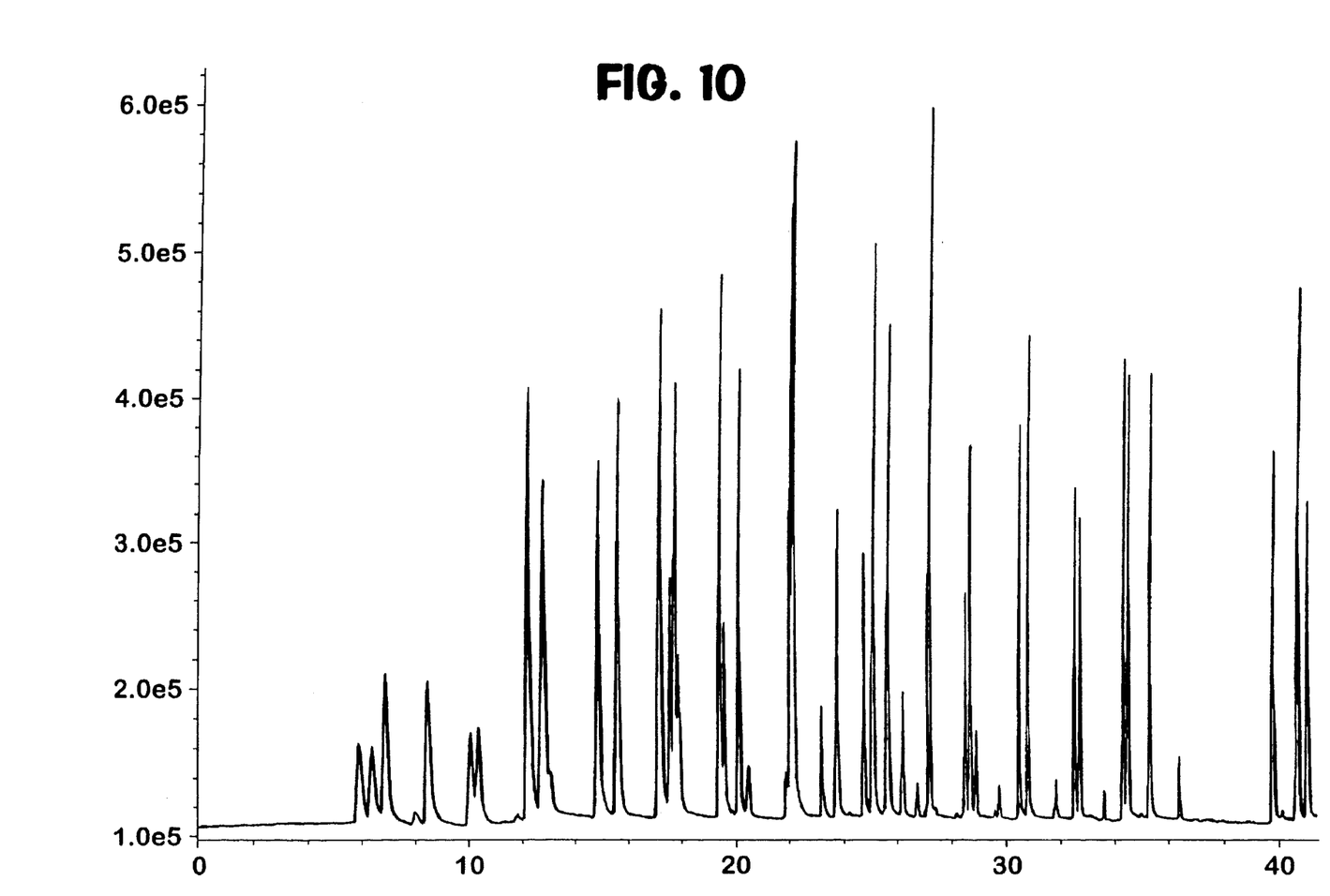
FIGS. 10 and 11 are a PID response and a halogen specific detector response, respectively, to EPA test series 502.2, using the tandem system of the present invention, with the inlet to the GC being plumbed with a purge and trap sample preconcentrator.
Figure 11:
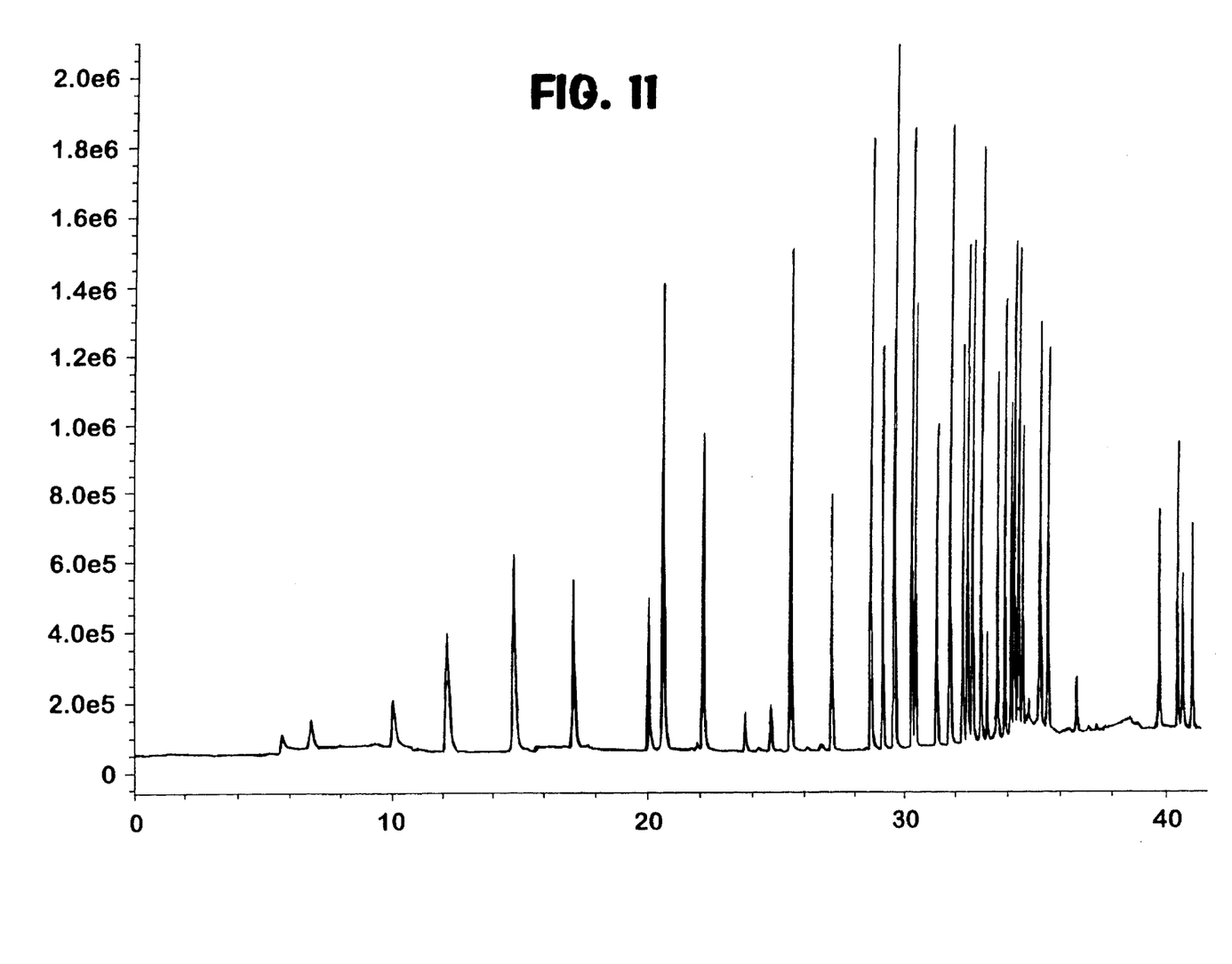

Additionally, a second auxiliary port (not shown) may be included in the coupling connector to provide air or oxygen to the inside of the jet without first passing through the PID. One reason for auxiliary port is to avoid running oxygen or air through the PID, which degrades PID performance. Thus, running air through the auxiliary port helps prevent sample pyrolysis (without air) inside the jet. Sample pyrolysis (without air) inside the jet can cause adsorption of the pyrolysis products, and thus cause band broadening and decreased performance. If that occurs, all of the sample may not reach the reactor core of the halogen specific detector in a timely manner. Another alternative is to provide a source of air or oxygen flow from the sweep gas inlet port through the exit port of the PID, although this can be detrimental to the PID performance. FIGS. 8 and 9 show the performance of the PID and halogen specific detector, respectively, having additional air flow through the PID.

Reactor body 17 houses reactor core 10 and probe assembly 18. The reactor body contains insulation surrounding the reactor core and probe assembly, and provides a seal surface between the reactor core and the coupling connector.

The reactor core 10 is an alumina tube, which preferably is high purity alumina. Preferably, the tube is approximately 4 inches in length, with an inner diameter of 0.1875 inches and an outer diameter of 0.250 inches.

Surrounding the outside of the reactor core is a heater wire 19, which is connected to a power source (not shown). The temperature of the reactor core is controlled by maintaining or varying the resistance of the heater wire and thus no temperature sensor is used to sense the temperature of the reactor core. Instead, the resistance of the heater wire may be calibrated with a thermocouple for precisely setting the reactor temperature. The heater wire uses DC current, generating electrical fields through the heater wire which contribute to the extraction field of the probe assembly. The heater wire is preferably platinum wire which allows heating up to 1200 degrees C., preferably between 1000 and 1200 degrees C., and most preferably 1100 degrees C. The responses of the PID and halogen specific detector in tandem at different temperatures is shown in FIGS. 2–7. Note the good time correlation of the peaks generated by the PID and halogen specific detectors.

In the reactor core, the sample is oxidatively pyrolyzed before reaching the probe assembly 18. The reactor core serves to maintain the temperature in the region where the oxidative pyrolysis occurs, as well as maintain the temperature of the sensing section 20 of the probe assembly. Preferably, the active heat region is 1.25 inches in length, positioned such that half of the reactor core is in the oxidative heating zone and the other half is capable of maintaining the same temperature in the sensing section of the probe assembly. The reactor core is preferably centered inside the reactor body 17 to minimize heat loss. It is desirable to maintain the same temperature in both of these sections of the reactor core to minimize thermal gradients and to maintain optimal performance of the detector.

The sensing section 20 of probe assembly 18 consists of an anode 21, a cathode 22, and a support rod 23. Support rod 23 is a source of alkali (typically an alkali glass ceramic, and preferably mullite). In operation (i.e., at its operating temperature of preferably at least 800 degrees C.), the surface of cathode 22 is coated with alkali metal from the support rod. Preferably, anode 21 and heater wire 19 are operatively connected to the same bias voltage.

The sensing section requires activation of the negatively biased platinum electrode (i.e., cathode 22) by alkali from support rod 23 to lower the work function of the platinum metal. Prior combustion of the sample in the reactor core is required to oxidize the analyte to carbon dioxide, water, and halogen atoms. Since the halogen atoms are in the gas phase, they also exist as dimers due to an equilibrium which exists. Increasing the reactor core temperature serves to drive the equilibrium to the dissociated halogen atoms. The mechanism for generation of the observed current when halogenated compounds are introduced into the reactor core is initial oxidative combustion, adsorption of the halogen onto the alkali activated cathode surface, thermionic electron emission by the cathode, followed by desorption of the halogen as either a neutral halogen atom, a negatively charged halogen atom, or an alkali halide. Thermionic electron emission is due to either further decrease of the work function by halogen adsorption, and/or increase of the local temperature of the cathode by electron attachment (i.e. the electron affinity of the halogen). Subsequent desorption of the halogen is by either negative surface ionization (i.e. release of the halogen as the gas phase halide) or reaction with the alkali activating the cathode to form an alkali halide which desorbs from the cathodic surface.

There are three mechanisms for generation of electrical current within the halogen specific detector of the present invention: positive surface ionization (PSI), negative surface ionization (NSI), and thermal electron emission (TEE).

Positive surface ionization occurs when the ionization potential of the neutral atom or molecule is less than the work function of the surface and the surface is positively polarized. The resulting thermal equilibrium between the neutral species and the ionized species is given by the Saha-Langmuir equation (Proceedings of the Royal Society of London, Ser. A, vol. 61, p. 107 (1925)):

$$n_+/n_o = \exp((\emptyset - IP)/kT)$$

where $n_+$ is the number of positively charged ions,
$n_o$ is the number of neutral species,
$\emptyset$ is the work function of the surface,
IP is the ionization potential of the neutral species,
k is the Boltzman constant, and
T is the temperature of the positively biased surface.

Negative surface ionization occurs when the electron affinity of the neutral atom or molecule approaches the work function of the surface and the surface is negatively polarized. The resulting thermal equilibrium between the neutral species and the ionized species is given by the following equation:

$$n_-/n_o = \exp(-(\emptyset - EA)/kT)$$

where $n_-$ is the number of negative ions produced,
$n_o$ is the number of neutral species remaining,
$\emptyset$ is the work function of the surface,
EA is the electron affinity of the neutral species,
k is the Boltzman constant, and
T is the temperature of the negatively biased surface.

Thermal electron emission occurs when electrons are emitted from surfaces into the gas phase. As the electron affinity approaches the work function, the probability of a negative ion being created increases rapidly. If the electron affinity exceeds that of the work function of the cathode (i.e. negatively biased surface), the excess energy can be imparted to the cathode surface, resulting in an increase in thermal electron emission due to a local temperature increase (which lasts until the surface thermally equilibrates with the body of the cathode).

Thermal electron emission (TEE) requires the surface to be negatively biased. The current generated by TEE is given by:

$$i = a_s A T^2 \exp(-\emptyset/kT)$$

where i is the current generated by TEE,
$a_s$ is the surface area of the negatively biased electrode,
A is a constant (1.20 A/mm$^2$K$^2$),
T is the temperature of the negatively biased surface,
$\emptyset$ is the work function of the negatively biased electrode, and
k is the Boltzman constant.

With the halogen specific detector of the present invention, only TEE can provide a sufficient quantity of electrons per halogen contact with an electrode surface (either positively or negatively biased surface). Thus, although a background current still exists due to alkali, the majority of the current in the halogen specific detector of the present invention is generated by TEE.

Mounted to the other end of support rod 23 is heat sink/connector assembly 24, which helps keep the connector (not shown) cool. The connector is typically connected to a current measuring device (not shown) and a voltage source for biasing the anode relative to the cathode.

Although variations in the embodiment of the present invention may not each realize all the advantages of the invention, certain features may become more important than others in various applications of the device. The invention, accordingly, should be understood to be limited only by the scope of the appended claims.

What is claimed is:

1. A system for detecting gaseous compounds comprising:

(a) a photoionization detector having an ionization chamber, means for introducing a sample into the ionization chamber, a light source, at least two electrodes, and at least one exit port, and means for measuring the current between the electrodes;

(b) a halogen specific detector having a reactor core, the reactor core housing a probe assembly comprising an anode, a cathode and support rod, the support rod consisting at least partially of an alkali material, a connection channel between the photoionization detector and the reactor core for introducing the sample from the photoionization detector into the reactor core, a wire around the reactor core for heating the reactor core sufficiently to oxidatively pyrolyze at least a portion of the sample, and sensing means for measuring charges being transferred between the anode and cathode; and (c) means for detecting gaseous compounds in the sample from the measured current and the measured charges.

* * * * *